United States Patent [19]

Klinkhammer

[11] Patent Number: 5,228,466
[45] Date of Patent: Jul. 20, 1993

[54] TOOTHBRUSH

[76] Inventor: Ronald W. Klinkhammer, 10231 63rd Ave. South, Seattle, Wash. 98179

[21] Appl. No.: 809,082

[22] Filed: Dec. 9, 1991

Related U.S. Application Data

[63] Continuation of Ser. No. 680,020, Apr. 2, 1991, abandoned, which is a continuation of Ser. No. 529,778, May 29, 1990, abandoned, which is a continuation of Ser. No. 228,503, Aug. 5, 1988, abandoned, which is a continuation-in-part of Ser. No. 145,771, Jan. 19, 1988, abandoned, which is a continuation of Ser. No. 664,487, Mar. 4, 1991, Pat. No. 5,137,039.

[51] Int. Cl.$^5$ ............................................. A45D 44/18
[52] U.S. Cl. ................................. 132/308; 132/309; 15/167.1; 15/167.2
[58] Field of Search ............. 132/308, 309; 128/62 A, 128/62 R; 15/167.1, 167.2, 159 A, DIG. 6

[56] References Cited

U.S. PATENT DOCUMENTS

| | | | |
|---|---|---|---|
| 301,644 | 7/1884 | Thompson | 128/62 A |
| 569,870 | 10/1896 | Hamilton | 15/167.1 |
| 1,389,624 | 9/1921 | Carroll | 15/167.2 |
| 1,709,262 | 4/1929 | Henderhan | 15/167.2 |
| 2,031,990 | 2/1936 | Turner | 15/104.94 |
| 2,117,174 | 5/1938 | Jones | 128/62 A |
| 2,139,245 | 12/1938 | Ogden | 128/62 A |
| 2,155,245 | 4/1939 | Sekine | 15/167.1 |
| 2,807,820 | 10/1957 | Dinhofer | 15/110 |
| 3,707,013 | 12/1972 | Erkers | 15/167.1 |
| 3,732,589 | 5/1973 | Burki | 15/22 R |
| 4,277,862 | 7/1981 | Weideman | 128/62 A |
| 4,449,266 | 5/1984 | Northemann et al. | 15/167.2 |
| 4,876,157 | 10/1989 | Barman | 15/167.2 |
| 4,972,542 | 11/1990 | Moshos et al. | 15/167.2 |

FOREIGN PATENT DOCUMENTS 0659502 6/1929 France.

*Primary Examiner*—John J. Wilson
*Assistant Examiner*—Jeffrey A. Smith
*Attorney, Agent, or Firm*—Christopher Duffy

[57] ABSTRACT

The brush 2' in FIGS. 8-11 is rod-like and a monolith of semi-rigid but resiliently flexible plastic material. It comprises elongated spaced parallel handle forming members 34 which are discrete from one another, but hingedly interconnected so as to be rotatable about axes 18' lying in a plane substantially coincident with the hinged connection 48 therebetween. Arms 40 project from the members, with the slot 50 therebetween, and wings 30' at the head 74 thereof. Bias inherent in the plastic, crosswise of the members 34 at the hinged connection, tends to flatten the device, as in FIGS. 9 and 10. But the bias is resiliently yieldable to the user's thumb and fingers so that the head 74 (or 30', 46, 48, 46, 30') can be pinched into the condition of FIG. 11 wherein the user must relatively forcibly wedge the tops of the teeth between the tooth cleaning sides 6' of the wings when the head is straddled about a row of teeth. Meanwhile, the midsection 48 of the head and the plastic portions 46 between it and the arms 40, form an articulated joint between the arms which is operable to preserve the straddling effect, yet allow the head to adjust to the varying diameters of the teeth when the head is translated along the row in engagement with the inside and outside faces of the teeth.

14 Claims, 2 Drawing Sheets

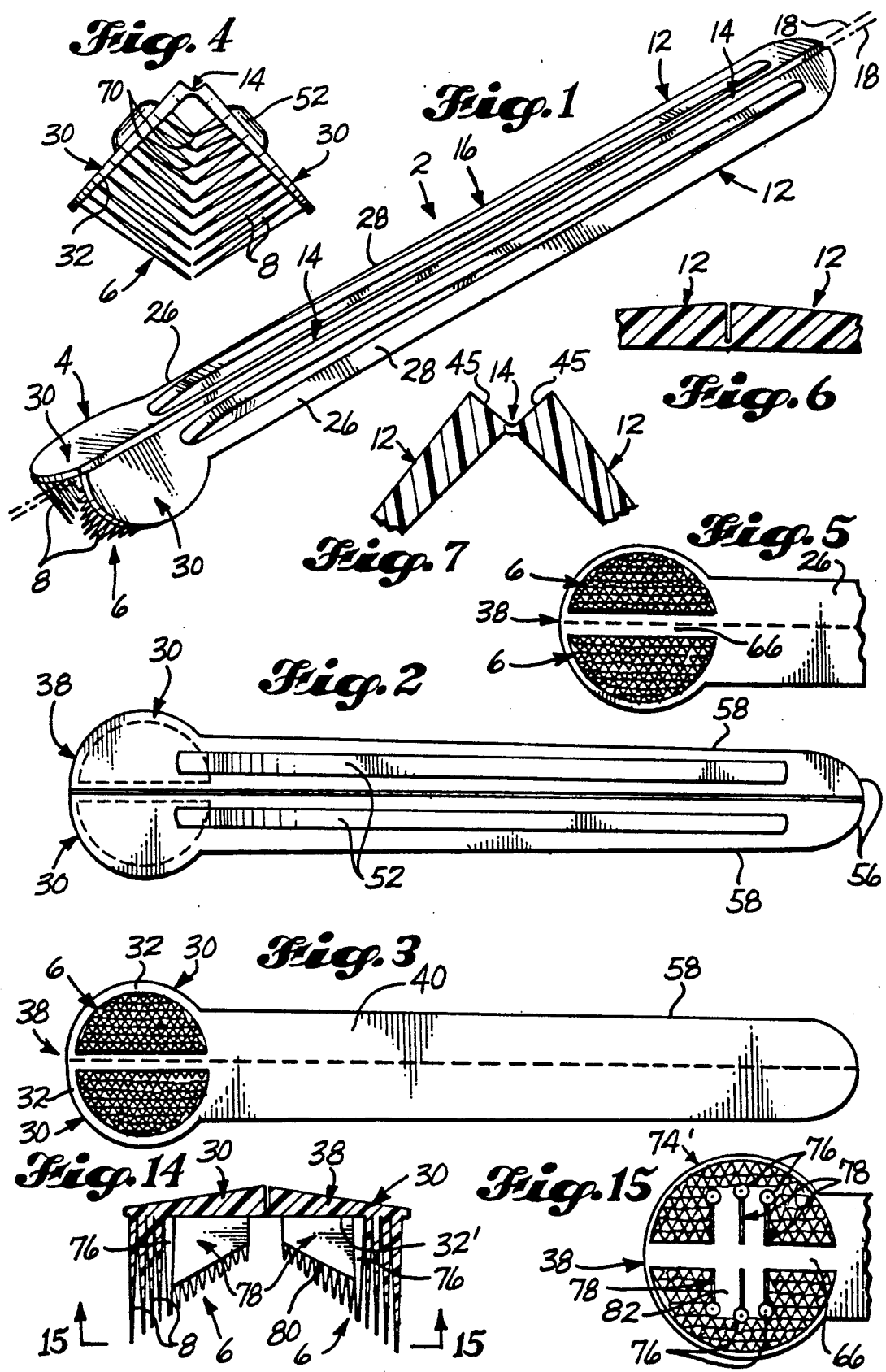

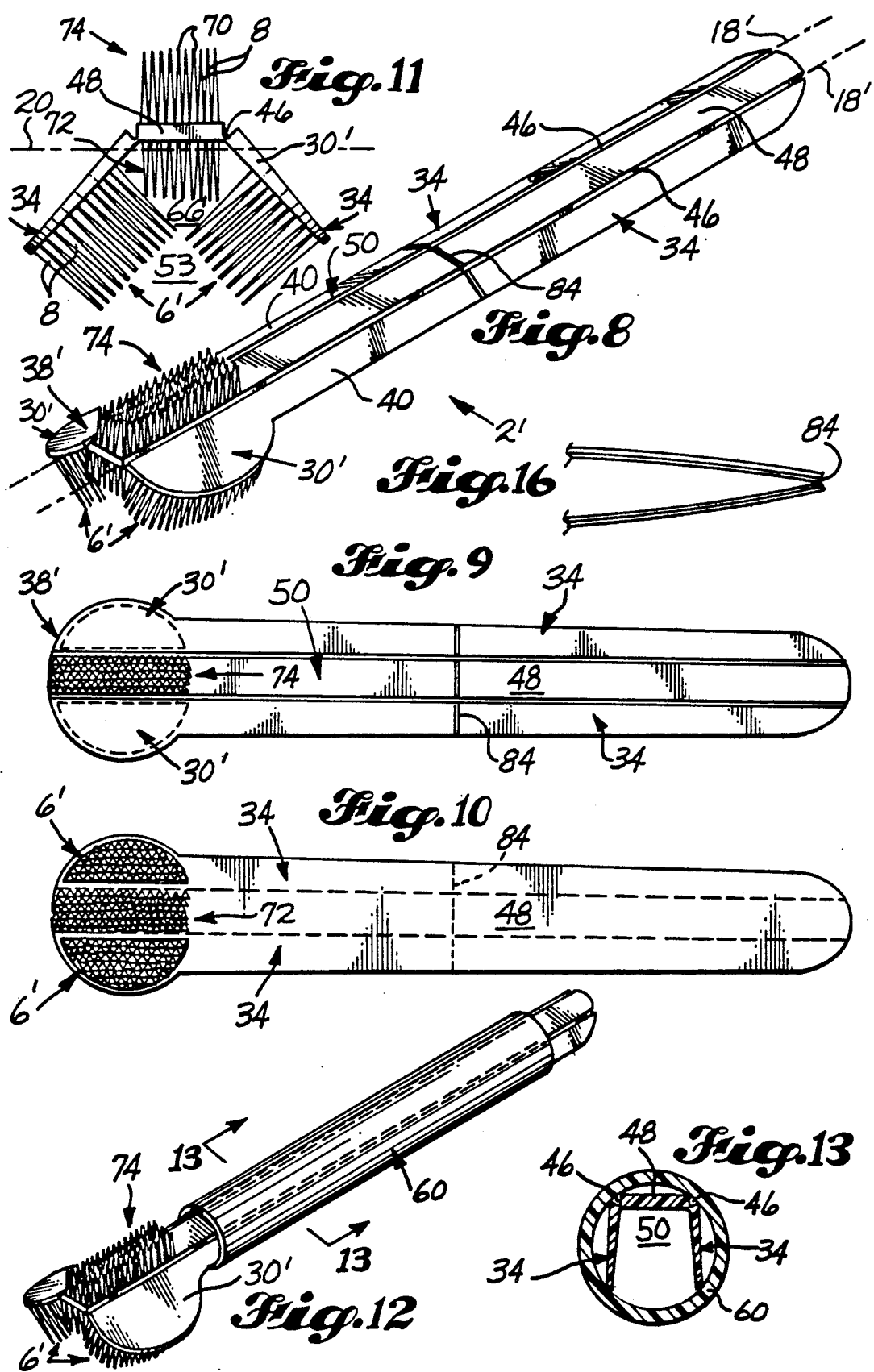

TOOTHBRUSH

RELATED APPLICATION

The present application is a continuation of application Ser. No. 680,020 filed Apr. 2, 1991, now abandoned, which in turn was a continuation of application Ser. No. 529,778, filed May 29, 1990, also abandoned, which in turn was a continuation of application Ser. No. 228,503, also abandoned, filed Aug. 5, 1988. Application Ser. No. 228,503 was a continuation in part of application Ser. No. 145,771, filed on Jan. 19, 1988, and now abandoned in favor of a continuation thereof, Ser. No. 664,487, filed on Mar. 4, 1991 (and now U.S. Pat. No. 5,137,039).

TECHNICAL FIELD

This invention relates to a tooth brush, and in particular to a straddle-type tooth brush.

BACKGROUND ART

In U.S. Pat. No. 2,807,820 to Dinhofer, the straddle-type tooth brush disclosed therein comprises an elongated rod-like device which comes in two parts, but when assembled, the device comprises a pair of elongated arms having outboard end portions and adapted for insertion in the mouth of the person whose teeth are to be cleaned, a tooth brushing implement that is connected with the arms for cleaning the teeth, and a handle that is operable to support the arms adjacent a row of teeth while the implement is applied thereto. The arms project from the distal end of the handle in generally spaced parallel relationship to one another, with an elongated slot extending therebetween, and are rigidly interconnected with the handle so as to form relatively rigid extensions of the same, longitudinally thereof. The implement comprises a foldable brush-forming head which is separate from the device, but operatively connected with the arms to straddle the slot at the outboard end portions of the arms on an axis of the implement extending from arm to arm crosswise the length of the slot. The brush-forming head has three sections in the body thereof comprising a pair of spaced wings, and a midsection in the space therebetween, which are serially interconnected with one another along the aforesaid axis of the implement. The head also has brush-forming means on corresponding sides of the wings, and when the head is folded and put to use, it is operatively arranged on the arms so that the wings are reentrantly folded about the midsection transverse the axis of the implement, with the brush-forming sides thereof folded relatively toward one another, but spaced apart from one another by a gap having a mouth opposite the midsection of the head for the introduction of the teeth to the gap. Additionally, the brush-forming head has added portions thereof, in the form of channeled sections, which are interposed between the respective wings and the midsection thereof, axially of the implement, to be used in mounting the implement on the arms when the wings have been reentrantly folded about the midsection as indicated.

DISCLOSURE OF THE INVENTION

The present invention relates to a similar straddle-type tooth brush, but one which is improved over Dinhofer's brush in that the rod-like device of the present invention is a monolith of a semi-rigid but resiliently flexible plastic material, and is molded or otherwise fabricated in two halves that are transversely foldable between a respectively flat condition in which the device can be packaged, stored and sold in compact form, and a reentrantly folded condition in which the head of the device is adapted for use as a straddle-type tooth cleaning head that has all of the features and advantages of the head disclosed in the aforementioned application Ser. No. 145,771 (now U.S. Pat. No. 5,137,039). This is to say that when the handle of the device is reentrantly folded into the operative condition and then held in one hand like a baton while the head of the device is straddled about a row of teeth and driven forward with the handle to translate it along the length of the row, the head will remain engaged with the inside and outside faces of the teeth, and will rake the gum lines of the teeth in its own right, without manipulation on the part of the user's hand, because of these features and advantages. While so engaged, moreover, and while raking the gum lines of the teeth, the head will adjust comfortably to the varying diameters of the teeth in the row.

When in the relatively flat condition, the halves of the device may also be foldable longitudinally thereof, so that it can be packaged in even more compact form when desired.

Often, the device is constructed as a disposable item. That is, it is constructed as one which can be put to use but a single time or two, and then thrown away because of its low price. In particular, the device may be molded from inexpensive polymeric material, and then packaged, marketed and priced in such inexpensive form, that the user will not hesitate to discard it after a single use or two. Hospitals, nursing homes and other health care facilities in particular, are in need of such a device to use on patients within their care.

According to the invention, the handle of the device comprises a pair of elongated handle-forming members which are discrete from one another, but are arranged in generally spaced parallel relationship to one another and hingedly interconnected with one another at the space therebetween so that they are rotatable in relation to one another about axes of rotation which extend between the members substantially parallel to the mutually adjacent sides thereof, and lie in a plane that substantially coincides with the hinged connection between the members. The arms of the device project from the distal ends of the handle-forming members in generally spaced parallel relationship to one another, with the slot extending therebetween, and are sufficiently rigidly interconnected with the handle-forming members to form relatively rigid extensions of the same, longitudinally thereof, which are conjointly rotatable with the handle-forming members about the aforesaid axes of rotation extending therebetween. Meanwhile, biasing means extending crosswise of the hinged connection between the handle-forming members, operate to bias the members to rotate in first angularly opposing directions about the axes therebetween, relatively toward first positions in which the members assume relatively low angles of incidence with the plane of the hinged connection therebetween, i.e., angles in which they tend toward a coplanar or flattened condition. The wings in the head of the device are connected with the outboard end portions of the arms so as to project laterally outwardly therefrom and rotate in conjunction with the arms about the axes of rotation extending between the members, including in the directions of the aforesaid first positions in which the members tend toward a coplanar or flattened condition. But the biasing means are resiliently yieldable to counterbiasing forces that are applied to the members in second axially opposing directions opposed to the aforesaid first directions about the axes between the members. And the midsection and added portions of the head of the device are disposed in the slot between the arms, and are flexibly interconnected with one another and with the arms so that when the counterbiasing forces are applied to the members in the second directions about the axes therebetween, and the members are rotated in the second directions to second positions in which the wings of the head are reentrantly folded about the midsection to such relatively high angles of incidence with the plane of the hinged connection that the user must relatively forcibly wedge the tops of the teeth between the tooth cleaning sides of the wings to straddle the head about a row of teeth, the midsection and added portions of the head form an articulated joint between the arms which is operable to preserve the counter bias of the forces on the wings axially of the implement, yet allow the head to adjust to the varying diameters of the teeth axially of the implement, when the head, after being straddled about a row of teeth, is translated along the length of the row in engagement with the opposing inside and outside faces of the teeth.

In many of the presently preferred embodiments of the invention, the midsection of the head of the device takes the form of a web-like member which is interposed in the slot between the arms, a tooth in width, and hingedly interconnected with the respective arms by the added portions of the head to form an articulated joint therebetween which is operable to preserve the counterbias of the forces on the wings axially of the implement as indicated. In some embodiments, the slot extends between the handle-forming members as well, and the axes of rotation of the handle-forming members are spaced apart from one another at the opposing sides of the slot, and the hinged connection between the handle-forming members takes the form of a web-like member which is interposed in the slot between the handle-forming members and hinged interconnected with the respective handle-forming members at the axes. In fact, in certain embodiments, the device has a single web-like member extending the length thereof, in the slot, which is hingedly interconnected with the respective handle-forming members at the axes to form the hinged connection therebetween, and hingedly interconnected with the respective arms by the added portions of the head to form the aforesaid articulated joint therebetween. In some of these, moreover, the added portions of the head are coextensive with the web-like member the full length of the slot, to form hinged connections between the web-like member and the handle-forming members as well.

In one group of the latter embodiments, the device has a pair of hinge forming grooves extending along the axes of rotation to subdivide the device into three hingedly interconnected sections, the edge forming sections of which, transversely of the axes, are inherently biased to assume the aforesaid first positions when the device is in the relaxed condition thereof. The wings of the head, meanwhile, project laterally outwardly from the edge forming sections of the device at the distal end portions of the edge forming sections, and the brush forming means are disposed on those sides of the wings which oppose one another when the edge forming sections of the device are rotated in the second directions about the axes.

Preferably, the brush further comprises means operatively interconnectable with the handle-forming members of the device to retain the members in the aforesaid second positions thereof when the counterbiasing forces are released therefrom. In certain of the presently preferred embodiments of the invention, for example, the retention means are separate from the device and take the form of an elongated tube which is slidably engageable about the pair of handle-forming members to retain the members in the aforesaid second positions thereof.

Preferably too, the handle-forming members of the device, and the hinged connection therebetween, have a hinge-forming groove extending thereacross, transverse the axes of rotation, to enable the relatively proximal and distal end portions of the handle-forming members to be reentrantly folded over onto one another, longitudinally of the device.

Typically, the brush forming means take the form of operatively mutually opposing first and second sets of bristle on the operatively opposing sides of the wings, which have a gap therebetween that coincides with a plane extending normal to the plane of the hinged connection and parallel to the axes of rotation. Moreover, the midsection of the head commonly has a third set of bristle thereon, opposite the mouth of the gap, as well as a fourth set of bristle thereon at the relatively outer periphery of the head.

BRIEF DESCRIPTION OF THE DRAWINGS

These features and advantages will be better understood by reference to the accompanying drawings which illustrate two straddle-type brushes, the second of which has a head that operates in accordance with the dictates of the aforementioned application Ser. No. 145,771 (now U.S. Pat. No. 5,137,039), and therefore, is preferred.

In the drawings:

FIG. 1 is a top perspective view of a brush which has a single hinge-forming groove along the top thereof;

FIG. 2 is a top plan view of the brush;

FIG. 3 is a plan view of the brush from the dorsal side thereof;

FIG. 4 is an end elevational view of the brush at the distal end thereof;

FIG. 5 is an enlarged plan view of the head of the brush from the dorsal side thereof;

FIG. 6 is a part cross sectional view of a molded brush at the time it is taken from the mold;

FIG. 7 is a part cross sectional view of the molded brush after it has undergone folding at the hinge thereof;

FIG. 8 is a top perspective view of a brush having a pair of spaced parallel hinge-forming grooves in the top thereof, with a web therebetween;

FIG. 9 is a top plan view of the brush in FIG. 8;

FIG. 10 is a plan view of the brush in FIGS. 8 and 9 from the dorsal side thereof;

FIG. 11 is an end elevational view of the brush in FIGS. 8-10 at the distal end thereof;

FIG. 12 is a top perspective view of the brush in FIGS. 8-11 when it has been equipped with a telescoping sheath to retain the handle-forming members in the rotated positions thereof when the counter-biasing forces are released from the members;

FIG. 13 is a cross section of FIG. 12 along the line 13—13 thereof;

FIG. 14 is a part cross sectional view of the head of the brush in FIGS. 1-7 when it has been modified to include gusseted stylus means in the opposing sets of bristle thereon;

FIG. 15 is a plan view of the modified head when seen along the line 15—15 of FIG. 14, and FIG. 16 is a part side elevational view of the brush in FIGS. 8-11, when it has been reentrantly folded, longitudinally thereof, to give it a more compact form.

BEST MODE FOR CARRYING OUT THE INVENTION

Referring to the drawings, it will be seen that the rod-like device 2 which forms the basic element of the tooth brush in FIGS. 1-7, is constructed from semi-rigid but resiliently flexible plastic material, and is monolithic in character. It also has halves 12 which are transversely foldable between a relatively flat condition (FIG. 6) in which the brush can be packaged, stored and sold in compact form, and a reentrantly folded condition (FIG. 7) in which the brush is adapted for use as a straddle-type tooth cleaning device, but not a device of the type disclosed by Dinhofer, nor a device of this type which in addition, has all of the features and advantages of the device disclosed in the aforementioned application Ser. No. 145,771 (now U.S. Pat. No. 5,137,039).

More specifically, the device 2 has an elongated body 16 of the aforesaid material, and a hinge-forming groove 14 running down the length of the body, at the center thereof, which leaves it bifurcated into halves 12. The halves operate as a pair of elongated handle-forming members 28 which are discrete from one another, but are arranged in generally spaced parallel relationship to one another and hingedly interconnected to one another at the groove 14 so that they can be rotated in relation to one another about axes 18 formed at the opposing sides 45 of the grooves. Moreover, because of the character of the plastic material and the manner in which it is fabricated, the members 28 are inherently biased in the angularly opposing upward directions about the axes 18, to assume relatively low angles of incidence to the plane of the groove 14 therebetween, that is, to assume positions in which the device 2 is relatively flat. Compare FIGS. 6 and 7. However, when the device is held in one hand in the manner of a baton, the bias on the members 28 is resiliently yieldable to the counterbiasing forces of the user's thumb and fingers in the angularly opposing downward directions (FIG. 7), to enable the members to be rotated to positions of relatively higher angles of incidence to the plane of the groove, so that the user can put the device to use as a toothbrush, though not one with as desireable a head as that in FIGS. 8-11, as shall be explained.

The groove 14 extends the full length of the device, from the proximal 56 to the distal ends 38 of the members 28, and at the distal end portions 26 of the members 28, the device has an ovate head 4 thereon which in turn has paddle-like wings 30 projecting laterally outwardly from the members, with phalanxes 6 of tooth brushing bristle 8 on those sides 32 of the wings 30 which oppose one another when the members are rotated in the downward directions about the axes 18. In the respective phalanxes 6, the bristle 8 have varying lengths, moreover, so that the two phalanxes 6 have oppositely inclined profiles at the tips thereof, relative to the dimensional planes of the wings 30. The inclination of the profiles is relatively downward into the gap or clearance 66 between the phalanxes, furthermore, so that the two phalanxes approach one another at an angle at approximately 90 degrees when the members 28 are rotated downward against the bias thereon to the positions of FIG. 4. This in turn inclines the respective sets of bristle 8 at approximately 45 degrees to the gum lines of a row of teeth, when the head 4 of the brush is straddled about the row and translated along the length of the row. The head 4 does not provide the action called for in application Ser. No. 145,771 (now U.S. Pat. No. 5,137,039), however, as shall be explained.

Commonly, the device 2 is molded from polymeric material which has an inherently resiliently yieldable bias across the groove 14 of the same when molded, so that the members 28 tend to assume a generally coplanar condition with one another as in FIG. 6. Preferably, however, the members 28 do not remain in a coplanar condition with one another when removed from the mold, so that when the user picks up the device 2 in one hand, he will find that the members are already somewhat opposed to his thumb and fingers, and can be readily "pinched" into operative condition without the necessity for bending them out of the coplanar condition first.

Preferably, too, the members 28 have reinforcing ribs 52 on the outer peripheries thereof to assure that the wings 30 are conjointly rotatable with the members about the axes 18. In fact, the ribs 52 commence on the distal end portions 26 of the members 28, and then taper inward along the lengths of the members to points adjacent the proximal ends 56 thereof. The ribs 52 may also taper sidewise toward the relatively remote edges 58 of the members, to assist the user in gripping the device with his thumb and fingers.

Turning now to the embodiment sown in FIGS. 8-11, it will be seen that the handle-forming members 34 of the device 2' now have a much wider slot 50 extending therebetween, for the full length of the device, and the hinged connection between the handle-forming members 34 takes the form of a web-like member 48 which is interposed in the slot 50, a tooth in width, and hingedly interconnected with the respective handle-forming members at axes of rotation 18' on the opposing sides of the slot. Once again, the device 2' is a monolith of a semi-rigid but resiliently flexible plastic material, as in FIGS. 1-7, and the members 34 are inherently biased in the angular opposing upward directions to assume relatively low angles of incidence to the plane of the web 48 therebetween. Moreover, once again, the bias on the members is resiliently yieldable to the counterbiasing forces of the user's thumb and fingers to enable the members 34 to be rotated in angularly opposing downward directions to positions in which the device 2' can be put to use as a tooth brush. However, in those positions, the device is more typical of the type shown in the aforementioned application Ser. No. 145,771 (now U.S. Pat. No. 5,137,039), in that, firstly, the distal end portions 40 of the handle-forming members 34 form a pair of elongated arms which project from the same in generally spaced parallel relationship to one another with the slot 50 extending therebetween, and with the head 74 of the device connected with the pair of arms 40 so as to straddle the slot 50 at the outboard end portions 38' of the arms on an axis 20 extending from arm to arm crosswise the length of the slot 50. See FIG. 11. Additionally, the head 74 now has three sections in the body thereof comprising a pair of spaced wings 30', and a midsection 48 in the space therebetween, which are serially interconnected with one another along the axis 20. The head 74 also has phalanxes 6' of tooth brushing bristle 8 on corresponding sides of the wings, and when it is folded, it is operatively arranged on the arms so that the wings 30' reentrantly fold about the full width of the midsection, transverse the axis 20 of the head, rather than about the sides 45 of a narrow groove 14, as in FIGS. 1–7. This means that when the tooth cleaning sides 6' of the wings approach one another in folding, they are not only spaced apart from one another by a deeper and more widely recessed tooth-sized gap 66' than was provided in FIGS. 1–7, having a mouth 53 opposite the midsection 48 for the introduction of the teeth to the gap, but in addition, the head 74 of the device operatively assumes a taco shell-shaped configuration in which the midsection 48 and the grooved hinge portions 46 of the head between the midsection 48 and the wings 30', are disposed in the slot 50 and flexibly interconnected with one another and with the arms 40 so that when the counterbiasing forces applied to the members 34 in the downward directions about the axes 18', reentrantly fold the wings 30' about the midsection 48 to such relatively high angles of incidencer with the plane of the midsection (See FIG. 13), that the user must relatively forcibly wedge the tops of the teeth between the tooth brushing sides 6' of the wings in the manner of the aforementioned application (now U.S. Pat. No. 5,137,039), to straddle the head 74 about a row of teeth, the midsection 48 and hinge portions 46 of the head form an articulated joint 46, 48 between the arms which is operable to preserve the counterbias on the wings axially of the head, yet allow the head 74 to adjust to the varying diameters of the teeth, when the head, after being straddled about the row of teeth, is translated along the length of the row in engagement with the opposing inside and outside faces of the teeth.

The device 2' in FIGS. 8–11, also has substantially collinear hinge forming grooves 84 thereacross, transverse the axes 18', and on the dorsal sides of the respective sections 34, 48, 34, whereby one end portion of the device can be folded over on the other, in the manner of FIG. 16, to render the device more compact longitudinally thereof, when the device is out of use.

Additionally, the head 74 of the device is equipped with an additional set 72 of bristle 8 on the inner periphery of the midsection 48, and a further set 70 of bristle 8 on the outer periphery of the midsection, which is directly opposed to that 72 on the inner periphery of the web.

As in application Ser. No. 145,771 (now U.S. Pat. No. 5,137,039), the wings of the head may be equipped with stylus-like means 76 that upstand within the sets 6' of bristle on the wings, and are sufficiently rigid and appropriately located on the inner peripheral faces 32' (FIG. 14) of the wings, to perform as picks that trace along the gum lines of a row of teeth to be cleaned, when the head 74' of the device (FIGS. 14 and 15) is straddled about the row and translated along the length of the row opposite the faces of the teeth, as explained in the co-pending application (now U.S. Pat. No. 5,137,039).

Preferably, the picks 76 are arranged in parallel rows on the opposite sides of the gap 66' (FIG. 15), and there are thin flanges 78 which extend relatively inwardly toward the gap from corresponding picks, and terminate at the gap, as seen in FIGS. 14 and 15. The flanges 78 provide fillet-like reinforcing gussets with which to stabilize the picks against splay when they are employed in raking the gum lines of the teeth to be cleaned.

Commonly, the flanges 78 are recessed below the profiles 80 of the sets of bristle 8 so that they do not interfere with the action of the bristle in the center region of the head as they provide the reinforcement indicated. In addition, when the picks 76 are arranged in two or more pairs of the same, the pairs are commonly spaced apart from one another in the center region of the head, and the spaces 82 between the respective pairs of flanges are freed of bristle on the opposing sides of the gap, as shown in FIG. 15.

When either device 2 or 2' is put to use, the user may choose to use further means such as the tube 60 seen FIGS. 12 and 13, to retain the members 28 or 34 in the reentrantly folded positions thereof. That is, before the user releases the members from the reentrantly folded condition thereof, he may telescopically engage the tube 60 about the members to provide a means for retaining the members in their respective positions when the counterbiasing forces of his thumb and forefingers are removed. The tube is shown as circular, but one with a more oblong cross section (not shown) may be employed, for example, for the embodiment of FIGS. 1–7.

I claim:
1. In a straddle-type tooth brush which comprises:
an elongated rod-like device which in turn comprises a pair of elongated arms having outboard end portions and adapted for insertion in the mouth of the person whose teeth are to be cleaned, a tooth brushing implement that is connected with the arms for cleaning the teeth, and a handle that is operable to support the arms adjacent a row of teeth while the tooth brushing implement is applied thereto,
the arms projecting from the distal end of the handle in generally spaced parallel relationship to one another, with an elongated slot extending therebetween, and the arms being rigidly interconnected with the handle so as to form relatively rigid extensions of the same, longitudinally thereof,
the tooth brushing implement comprising a brush-forming head which is connected with the arms and straddles the slot at the outboard end portions of the arms on an axis of the tooth brushing implement extending from arm to arm crosswise the length of the slot,
the brush-forming head having three sections in the body thereof comprising a pair of spaced wings, and a midsection in the space therebetween, which are serially interconnected with one another along the aforesaid axis of the tooth brushing implement,
the head also having brush-forming means on corresponding sides of the wings and being arranged on the arms so that the wings are reentrantly folded about the midsection transverse the axis of the tooth brushing implement, with the brush-forming sides thereof folded relatively toward one another, but spaced apart from one another by a gap having a mouth opposite the midsection of the head for the introduction of the teeth to the gap, and
the brush-forming head having added portions thereof which are interposed between the respective wings and the midsection thereof, axially of the tooth brushing implement,
the improvement wherein:
the rod-like device is a monolith of a semi-rigid but resiliently flexible plastic material, the handle of the device comprises a pair of elongated handle-forming members which are discrete from one another, but are arranged in generally spaced parallel relationship to one another and hingedly interconnected with one another at the space therebetween so that they are rotatable in relation to one another about axes of rotation which extend between the handle forming members substantially parallel to the mutually adjacent sides thereof, and lie in a plane that substantially coincides with the hinged connection between the members, the arms of the device project from the distal ends of the handle-forming members in generally spaced parallel relationship to one another, with the slot extending therebetween, and are sufficiently rigidly interconnected with the handle forming members to form relatively rigid extensions of the same, longitudinally thereof, which are conjointly rotatable with the handle forming members about the aforesaid axes of rotation extending therebetween, biasing means extending crosswise of the hinged connection between the handle forming members, operate to bias the members to rotate in first angularly opposing directions about the axes therebetween, relatively toward first positions in which the members assume relatively low angles of incidence with the plane of the hinged connection therebetween, the wings in the head of the device are connected with the outboard end portions of the arms so as to project laterally outwardly therefrom and rotate in conjunction with the arms about the axes of rotation extending between the handle forming members, the biasing means are resiliently yieldable to counterbiasing forces that are applied to the handle forming members in second axially opposing directions opposed to the aforesaid first directions about the axes between the members, and the midsection and added portions of the head of the device are disposed in the slot between the arms, and are flexibly interconnected with one another and with the arms so that when the counterbiasing forces are applied to the handle forming members in the second directions about the axes therebetween, and the members are rotated in the second directions to second positions in which the wings of the head are reentrantly folded about the midsection to such relatively high angles of incidence with the plane of the hinged connection that the user must relatively forcibly wedge the tops of the teeth between the tooth cleaning sides of the wings to straddle the head about a row of teeth, the midsection and added portions of the head form an articulated joint between the arms which is operable to preserve the counterbias of the forces on the wings axially of the tooth brushing implement, yet allow the head to adjust to the varying diameters of the teeth axially of the tooth brushing implement, when the head, after being straddled about a row of teeth, is translated along the length of the row in engagement with the opposing inside and outside faces of the teeth.

2. The straddle-type tooth brush according to claim 1 wherein the midsection of the head of the device takes the form of a web-like member which is interposed in the slot between the arms, a tooth in width, and hingedly interconnected with the respective arms by the added portions of the head to form an articulated joint therebetween which is operable to preserve the counterbias of the forces on the wings axially of the tooth brushing implement as indicated.

3. The straddle-type tooth brush according to claim 2 wherein the slot extends between the handle-forming members as well, and the axes of rotation of the handle-forming members are spaced apart from one another at the opposing sides of the slot, and the hinged connection between the handle-forming members takes the form of a web-like member which is interposed in the slot between the handle-forming members and hingedly interconnected with the respective handle-forming members at the axes.

4. The straddle-type tooth brush according to claim 3 wherein the device has a single web-like member extending the length thereof, in the slot, which is hingedly interconnected with the respective handle-forming members at the axes to form the hinged connection therebetween, and hingedly interconnected with the respective arms by the added portions of the head to form the aforesaid articulated joint therebetween.

5. The straddle-type tooth brush according to claim 4 wherein the added portions of the head are coextensive with the web-like member the full length of the slot, to form hinged connections between the web-like member and the handle-forming members as well.

6. The straddle-type tooth brush according to claim 1 wherein the device has a pair of hinge-forming grooves extending along the axes of rotation to subdivide the device into three hingedly interconnected sections, the edge-forming sections of which, transversely of the axes, are inherently biased to assume the aforesaid first positions when the device is in the relaxed condition thereof, the wings of the head projecting laterally outwardly from the edge-forming sections of the device at the distal end portions of the edge-forming sections, and the brush forming means being disposed on those sides of the wings which opposite one another when the edge-forming sections of the device are rotated in the second directions about the axes.

7. The straddle-type tooth brush according to claim 1 further comprising means operatively interconnectable with the handle-forming members of the device to retain the handle forming members in the aforesaid second positions thereof when the counterbiasing forces are released therefrom.

8. The straddle-type tooth brush according to claim 7 wherein the retention means are separated from the device and take the form of an elongated tube which is slideably engageable about the pair of handle-forming members to retain the members in the aforesaid second positions thereof.

9. The straddle-type tooth brush according to claim 1 wherein the handle-forming members of the device, and the hinged connection therebetween, have a hinge-forming groove thereacross, transverse the axes of rotation, to enable the relatively proximal and distal end portions of the handle-forming members to be reentrantly folded over onto one another, longitudinally of the device.

10. The straddle-type tooth brush according to claim 1 wherein the brush forming means take the form of operatively mutually opposing first and second sets of bristle on the operatively opposing sides of the wings, which have a gap therebetween which coincides with a plane extending normal to the plane of the hinged connection and parallel to the axes of rotation.

11. The straddle-type tooth brush according to claim 1 wherein the midsection of the head has a third set of bristle thereon, opposite the mouth of the gap.

12. The straddle-type tooth brush according to claim 11 wherein the midsection of the head has a fourth set of bristle thereon at the relatively outer periphery of the head.

13. The straddle type toothbrush according to claim 1 wherein in the first positions of the handle forming members, the monolith is foldable about an axis extending crosswise the axes of rotation of the handle forming members so that the monolith can be reduced to a more compact form.

14. The straddle type toothbrush according to claim 13 wherein the monolith has a body and the crosswise axis extends within the body of the monolith so that the relatively proximal and distal end portions of the respective handle forming members can be folded over onto one another longitudinally of the device.

* * * * *